(12) United States Patent
Kamihara

(10) Patent No.: US 8,282,544 B2
(45) Date of Patent: Oct. 9, 2012

(54) ENDOSCOPE SYSTEM

(75) Inventor: Yasuhiro Kamihara, Tokyo (JP)

(73) Assignee: Olympus Corporation, Tokyo (JP)

( * ) Notice: Subject to any disclaimer, the term of this patent is extended or adjusted under 35 U.S.C. 154(b) by 1469 days.

(21) Appl. No.: 11/888,456

(22) Filed: Aug. 1, 2007

(65) Prior Publication Data

US 2008/0039696 A1    Feb. 14, 2008

(30) Foreign Application Priority Data

Aug. 8, 2006   (JP) .................................. 2006-215409

(51) Int. Cl.
*A61B 1/06* (2006.01)
*A61B 1/00* (2006.01)
(52) U.S. Cl. ........................................ 600/160; 600/103
(58) Field of Classification Search .................. 600/103, 600/108, 118, 129, 160, 172–173, 175–176, 600/178, 181
See application file for complete search history.

(56) References Cited

U.S. PATENT DOCUMENTS

| 7,187,453 | B2 * | 3/2007 | Belleville ...................... 356/504 |
| 7,447,534 | B1 * | 11/2008 | Kingsley et al. ............... 600/372 |
| 2005/0027166 | A1 * | 2/2005 | Matsumoto et al. .......... 600/162 |

FOREIGN PATENT DOCUMENTS

JP    2802061    7/1998

OTHER PUBLICATIONS

Abstract only 63-271308 dated Nov. 9, 1988.

* cited by examiner

*Primary Examiner* — Philip R Smith
(74) *Attorney, Agent, or Firm* — Scully, Scott, Murphy & Presser, P.C.

(57) ABSTRACT

Spectral characteristics are controlled with high accuracy using a variable-spectrum device provided at the tip of a long insertion portion of an endoscope, thereby acquiring a sharp observation image. An endoscope system, at least a portion of which is to be inserted into the body cavity of a living organism and which acquires an image of an observation target in the body cavity, includes, at a leading end of the portion inserted into the body cavity, a variable-spectrum device whose spectral characteristics are changed by changing a gap between two facing optical elements that are separated by the gap; an actuator that changes the gap between the two optical elements in accordance with an input driving signal; a sensor that detects the gap between the two optical elements; and an electrical circuit to which the output of the sensor is input, which includes an active device, and which outputs an electrical signal corresponding to the output of the sensor.

16 Claims, 10 Drawing Sheets

ENDOSCOPE SYSTEM

BACKGROUND OF THE INVENTION

1. Field of the Invention

The present invention relates to an endoscope system.

This application is based on Japanese Patent Application No. 2006-215409, the content of which is incorporated herein by reference.

2. Description of Related Art

A known technique for changing the wavelength characteristics of observation light or illumination light involves disposing an etalon, in which distances between a plurality of optical elements can be varied by driving means composed of a piezoelectric element, in at least one of an image-acquisition optical system and an illumination optical system provided at a tip of an endoscope system (see, for example, Publication of Japanese Patent No. 2802061).

Spectroscopic information of a living organism or the like can be obtained by employing the technique disclosed in Publication of Japanese Patent No. 2802061. In the etalon disclosed in this patent document, driving means composed of a piezoelectric element that varies the distances between two or more optical elements is provided between the optical elements.

Etalons change their transmission characteristics using an optical interference effect. Accordingly, it is necessary to control the spectral characteristics with high accuracy by precisely controlling the distance between adjacent optical elements while keeping the distance close to about the coherence length of the light or less. In this case, only supplying a driving signal that is determined in advance in accordance with the distance between the optical elements to the driving means composed of the piezoelectric element is not sufficient to control the spectral characteristics with high accuracy.

An insertion portion of an endoscope that is inserted in a body cavity has an extremely small diameter and generally has a length of about 1 m or more. In addition, transmission lines of the driving voltage for operating the driving means composed of the piezoelectric element, transmission lines of signals of an image-acquisition device, and the like are disposed close together. Therefore, it is necessary to control the spectral characteristics with high accuracy while suppressing the effects of noise due to these electrical signals.

BRIEF SUMMARY OF THE INVENTION

The present invention provides the following solutions.

An aspect of the present invention provides an endoscope system, at least a portion of which is to be inserted into the body cavity of a living organism and which acquires an image of an observation target in the body cavity, includes, at a leading end of the portion inserted into the body cavity, a variable-spectrum device whose spectral characteristics are changed by changing a gap between two facing optical elements that are separated by the gap; an actuator that changes the gap between the two optical elements in accordance with an input driving signal; a sensor that detects the gap between the two optical elements; and an electrical circuit to which the output of the sensor is input, which includes an active device, and which outputs an electrical signal corresponding to the output of the sensor.

In the above aspect, the electrical circuit may include an amplifying circuit. Alternatively, the electrical circuit may include a buffer circuit.

In the above aspect, the sensor may include a plurality of electrodes provided on the two optical elements, and the gap between the two optical elements may be detected by detecting the capacitance between the electrodes.

In the above aspect, the sensor may include a coil provided on one of the two optical elements and a metal plate provided on the other optical element, and the gap between the two optical elements may be detected by detecting the impedance of the coil.

In the above aspect, the actuator may be composed of a piezoelectric element.

In the above aspect, the endoscope system may further include a photoelectric transducer facing the variable-spectrum device.

In the above structure, the photoelectric transducer may be a light source that converts an electrical signal into light.

In the above structure, the photoelectric transducer may be a light-receiving device that converts light into an electrical signal.

In the above aspect, the leading end may be disposed closer to a tip than a portion that can be bent in order to change the orientation of the tip of the insertion portion.

In the above aspect, the electrical circuit may be disposed adjacent to the variable-spectrum device.

In the above aspect, the electrical circuit may be disposed closer to the rear end of the insertion portion than the variable-spectrum device.

In the above aspect, the electrical circuit may be disposed at a position that is shifted from the variable-spectrum device in the axial direction of the insertion portion and that overlaps the variable-spectrum device in the radial direction of the insertion portion.

In the above aspect, a plurality of actuators may be disposed around the axis of the insertion portion at intervals in the circumferential direction thereof, and the electrical circuit may be disposed in a space between the actuators.

In the above structure, the electrical circuit may be provided on a substrate of the photoelectric transducer.

In the above structure, the electrical circuit may be disposed closer to the leading end of the insertion portion than the photoelectric transducer.

In the above aspect, one of the two optical elements may be fixed to the portion inserted into the body cavity, and the electrical circuit may be fixed to the one fixed optical element.

DETAILED DESCRIPTION OF THE INVENTION

An endoscope system 1 according to a first embodiment of the present invention will now be described with reference to FIGS. 1 to 5.

Figure 1:
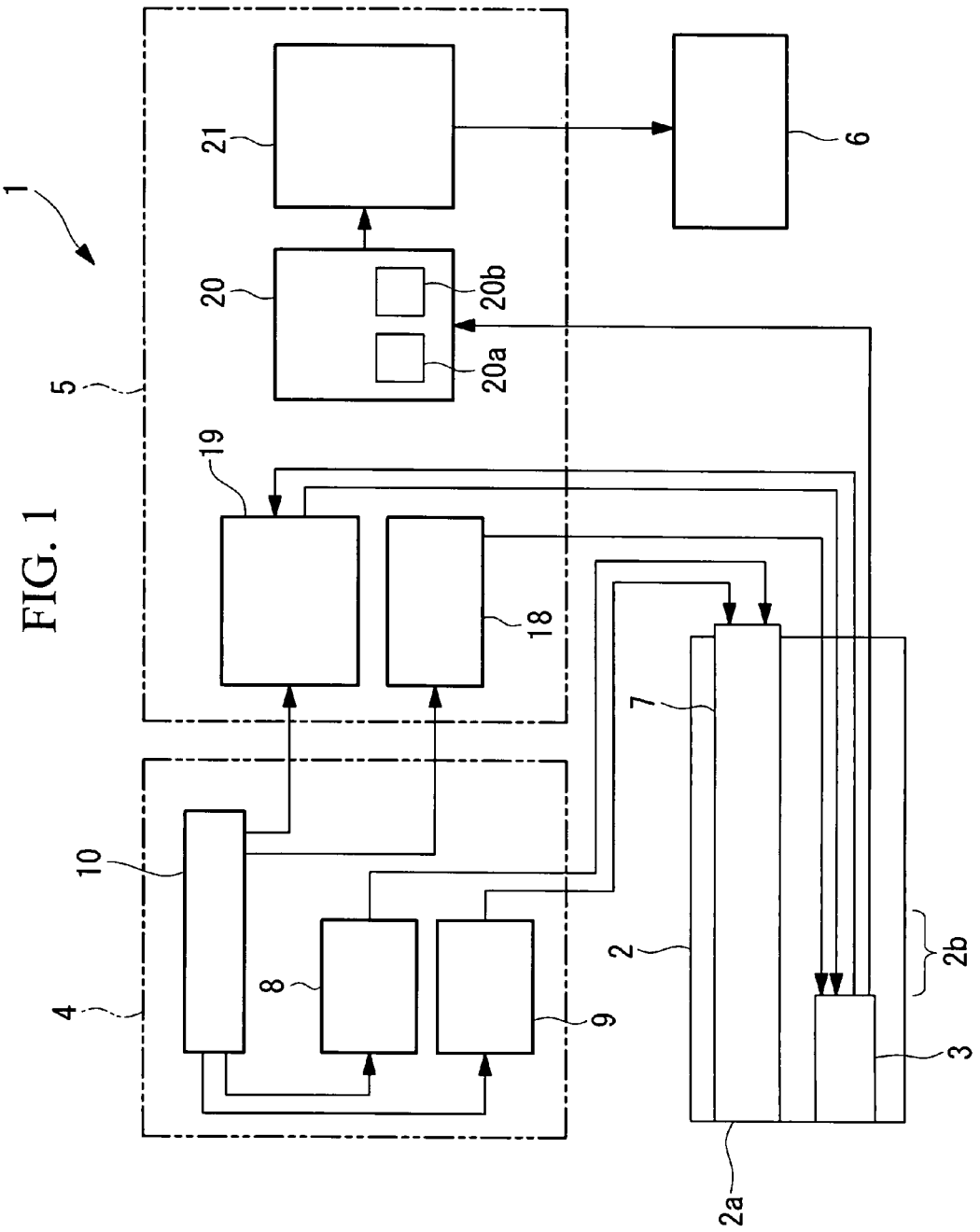
FIG. 1 is a block diagram showing the overall structure of an endoscope system according to a first embodiment of the present invention.

As shown in FIG. 1, the endoscope system 1 includes an insertion portion 2 that is inserted into the body cavity of a living organism, an image-acquisition unit 3 disposed in the insertion portion 2, a light source unit 4 that emits a plurality of types of light, a control unit 5 that controls the image-acquisition unit 3 and the light source unit 4, and a display unit 6 that displays an image acquired by the image-acquisition unit 3.

The insertion portion 2 has an extremely small outer diameter so as to be inserted into the body cavity of an organism. The image-acquisition unit 3 and a light guide 7 that transmits light from the light source unit 4 to a tip 2a are provided in the insertion portion 2.

The light source unit 4 includes an illumination light source 8, an excitation light source 9, and a light source control circuit 10. The illumination light source 8 emits illumination light for illuminating an observation target in the body cavity to obtain reflected light that is reflected at the observation target and returns therefrom. The excitation light source 9 emits excitation light that is irradiated on the observation target in the body cavity to excite a fluorescent material present in the observation target, generating fluorescence. The light source control circuit 10 controls these light sources 8 and 9.

The illumination light source 8 includes, for example, a xenon lamp and a band-pass filter (not shown) in combination; the 50% transmission range of the band-pass filter is in the range of 430 to 460 nm. That is, as shown in FIG. 3, the light source 8 generates illumination light in a wavelength band of 430 to 460 nm.

Figure 3:
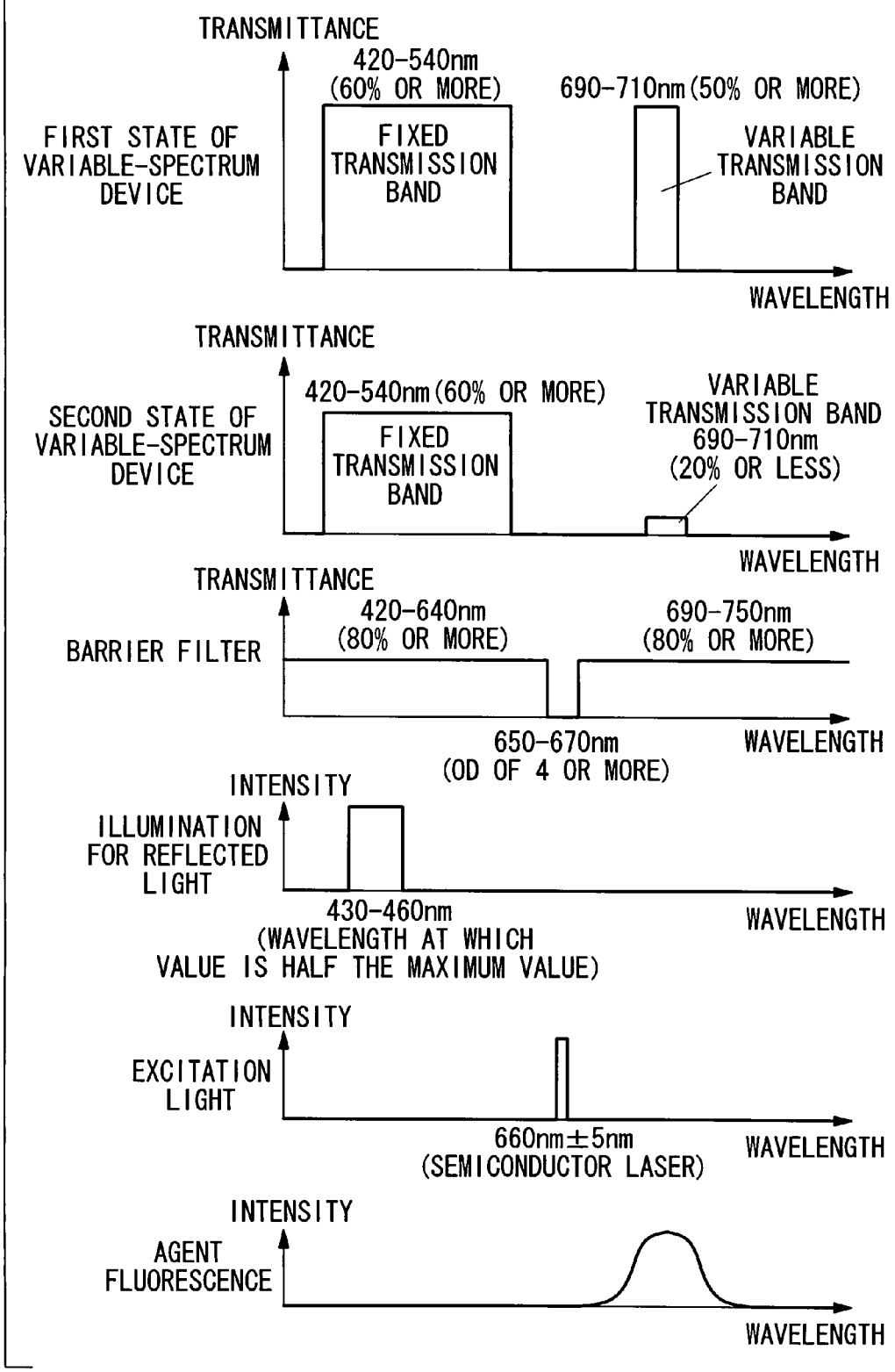
FIG. 3 includes graphs showing a transmittance characteristic of a variable-spectrum device provided in the image-acquisition unit shown in FIG. 2.

The excitation light source 9 is, for example, a semiconductor laser that emits excitation light having a peak wavelength of 660±5 nm, as shown in FIG. 3. The excitation light having this wavelength can excite fluorescent agent such as Cy 5.5 (registered trademarks of GE Healthcare, Inc. (formerly Amersham Biosciences Corp.)) and Alexa Fluor 700 (manufactured by Molecular Probes, Inc.).

The light source control circuit 10 alternately switches on and off the illumination light source 8 and the excitation light source 9 at a predetermined timing according to a timing chart described below.

The image-acquisition unit 3 is disposed at an end portion of the insertion portion 2. The end portion of the insertion portion 2 is located, for example, on the tip 2a side of the central position of the insertion portion 2 in the longitudinal direction, and more preferably, on the tip 2a side of a bending portion 2b that can be bent in order to change the orientation of the tip 2a of the insertion portion 2.

Figure 2:
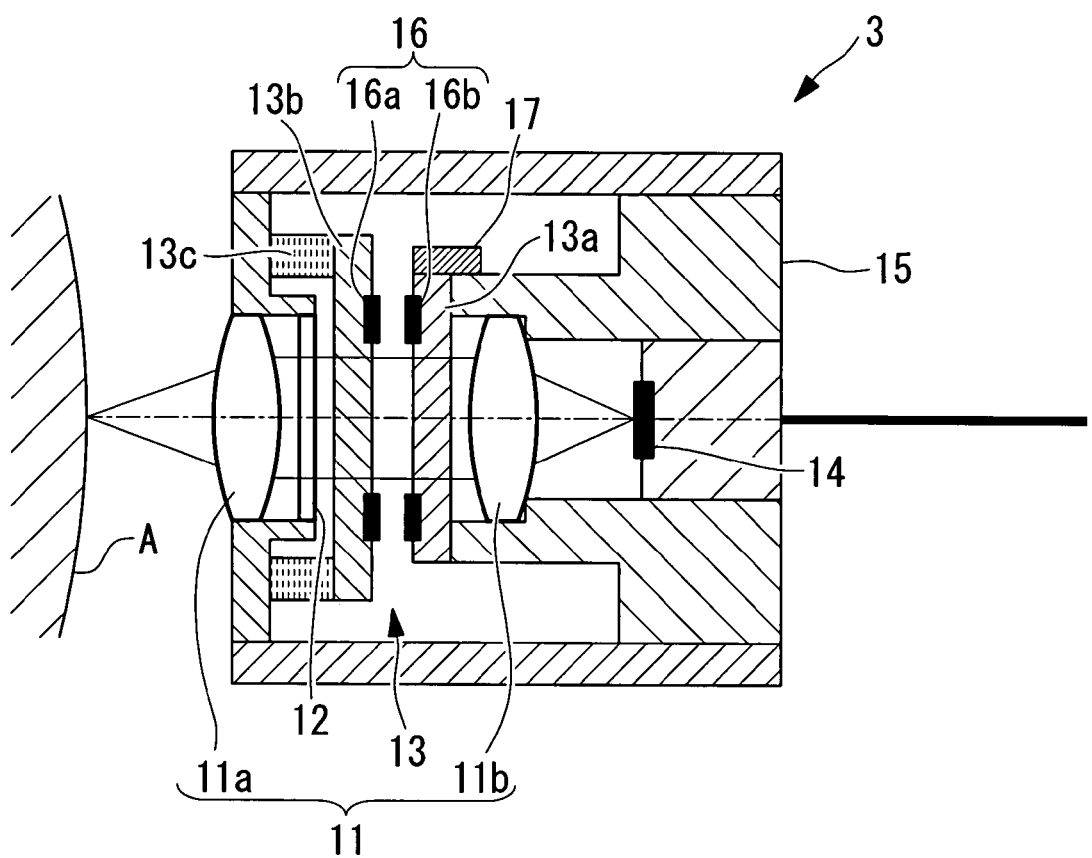
FIG. 2 is a longitudinal sectional view that schematically shows an image-acquisition unit of the endoscope system shown in FIG. 1.

As shown in FIG. 2, the image-acquisition unit 3 includes an image-acquisition optical system 11 having lenses 11a and 11b that collect and condense light incident from an observation target A, a barrier filter 12 that blocks excitation light incident from the observation target A, a variable-spectrum device 13 whose spectral characteristics are changed by the operation of the control unit 5, an image-acquisition device (photoelectric transducer: light-receiving device) 14 that acquires the light collected and condensed by the image-acquisition optical system 11 and that converts the light into electrical signals, and a frame structure 15 that supports these components.

The variable-spectrum device 13 is an etalon optical filter including two disc-shaped optical elements 13a and 13b that are disposed in parallel with a distance therebetween and that have reflective films on the surfaces facing each other, and actuators 13c that change the distance between the optical elements 13a and 13b. The optical element 13a is directly fixed to the frame structure 15, and the optical element 13b is attached to the frame structure 15 via the actuators 13c.

The actuators 13c are multilayer piezoelectric elements and are provided at four positions around the edge of the optical element 13b in the circumferential direction at regular intervals.

In this variable-spectrum device 13, the distance between the optical elements 13a and 13b can be changed by the operation of the actuators 13c, thereby changing the wavelength band of light passing in the axial direction.

More specifically, as shown in FIG. 3, the variable-spectrum device 13 has a transmittance-versus-wavelength characteristic having two transmission bands, i.e., a fixed transmission band and a variable transmission band. The incident light is constantly transmitted in the fixed transmission band regardless of the state of the variable-spectrum device 13. On the other hand, the transmittance characteristic in the variable transmission band is changed depending on the state of the variable-spectrum device 13. Sensors 16 for detecting the distance between the optical elements 13a and 13b are provided on the two optical elements 13a and 13b of the variable-spectrum device 13. The sensors 16 are capacitance-type sensors and each include a plurality of sensor electrodes 16a and 16b that are provided at positions facing each other at the periphery outside an effective optical diameter B (see FIG. 7B) of the optical elements 13a and 13b. The sensor electrodes 16a and 16b are provided at four positions at regular intervals around the circumferential direction of the periphery of the optical elements 13b and 13a, respectively. A metal film can be used for the sensor electrodes 16a and 16b.

Figure 5:
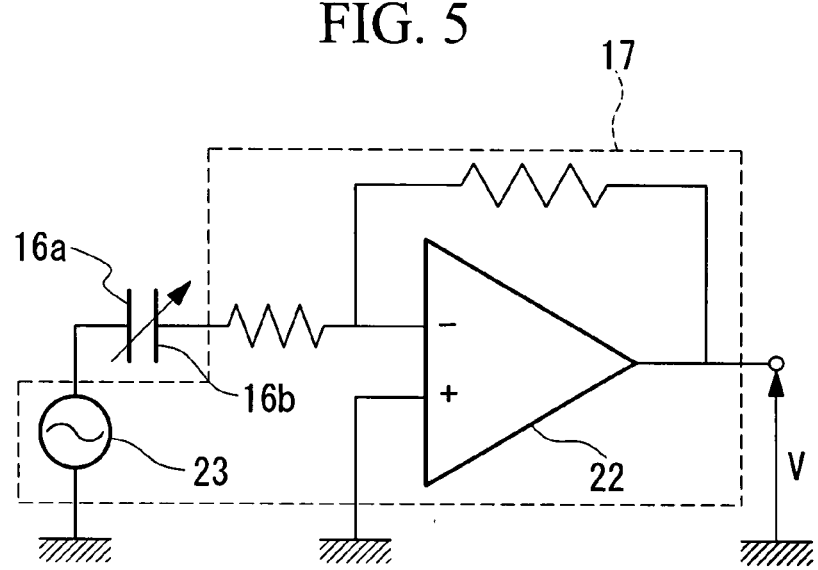
FIG. 5 is a diagram showing an electrical circuit that amplifies signals of a sensor of the variable-spectrum device provided in the image-acquisition unit shown in FIG. 2.

The capacitance-type sensors utilize a characteristic whereby the capacitance between the sensor electrodes 16a and 16b changes in inverse proportion to the distance between the surfaces. An electrical circuit 17 is connected to the sensor electrodes 16a and 16b. For example, as shown in FIG. 5, in the electrical circuit 17, an alternating current is supplied to the sensor electrodes 16a and 16b, and the capacitance between the sensor electrodes 16a and 16b, which is determined according to the distance between the optical elements 13a and 13b, is converted into a voltage signal V. The voltage V is then amplified and output. In FIG. 5, reference numeral 22 indicates an operational amplifier, which is an active device, and reference numeral 23 indicates an AC power supply. The electrical circuit 17 is fixed to the optical element 13a, which is fixed to the frame structure 15.

In fluorescence observation, since the resulting fluorescence intensity is generally very weak, the transmission efficiency of the optical system is very important. In the etalon-type variable-spectrum device 13, when the reflective films are disposed in parallel, a high transmittance can be obtained. However, if there is any error in the adjustment of the parallelism, the transmittance is markedly decreased. Accordingly, the variable-spectrum device 13 used in the image-acquisition unit 3 for fluorescence observation preferably includes a plurality of sensors 16 and has a plurality of degrees of freedom for driving so as to adjust any errors in the inclination of the two optical elements 13a and 13b when the distance therebetween is changed.

By performing feedback control of the driving signals to the actuators 13c on the basis of the signals from the sensor electrodes 16a and 16b, the accuracy controlling the transmittance characteristic can be improved.

In this embodiment, the variable-spectrum device 13 has a variable transmission band in a wavelength band (e.g., ranging from 690 to 710 nm) including a wavelength (e.g., the wavelength shown in FIG. 3) of fluorescence emitted by excitation of a fluorescent agent by excitation light (agent fluorescence). The variable-spectrum device 13 is switched between two states in accordance with control signals from the control unit 5.

A first state is a state in which the transmittance in the variable transmission band is increased to 50% or more, and the agent fluorescence is transmitted. A second state is a state in which the transmittance in the variable transmission band is decreased to 20% or less, and the agent fluorescence is blocked.

In the second state, the agent fluorescence may be blocked by changing the wavelength band of the variable transmission band from that of the first state.

The fixed transmission band is located, for example, in the range of 420 to 540 nm and is designed to have an average transmittance of 60% or more.

The fixed transmission band is located in a wavelength band including the wavelength of reflected light of the illumination light so that the reflected light is transmitted toward the image-acquisition device 14 in either the first state or the second state.

As shown in FIG. 3, the barrier filter 12 has a transmittance of 80% or more in a wavelength band of 420 to 640 nm, an optical density (OD) value of 4 or more (=transmittance of $1 \times 10^{-4}$ or less) in a wavelength band of 650 to 670 nm, and a transmittance of 80% or more in a wavelength band of 690 to 750 nm.

As shown in FIG. 1, the control unit 5 includes an image-acquisition-device driving circuit 18 that drives and controls the image-acquisition device 14, a variable-spectrum-device control circuit 19 that drives and controls the variable-spectrum device 13, a frame memory 20 that stores image information acquired by the image-acquisition device 14, and an image-processing circuit 21 that processes the image information stored in the frame memory 20 and outputs the processed image information to the display unit 6.

The image-acquisition-device driving circuit 18 and the variable-spectrum-device control circuit 19 are connected to the light source control circuit 10 and drive and control the image-acquisition device 14 and the variable-spectrum device 13, respectively, in synchronization with the switching between the illumination light source 8 and the excitation light source 9 performed by the light source control circuit 10.

Figure 4:
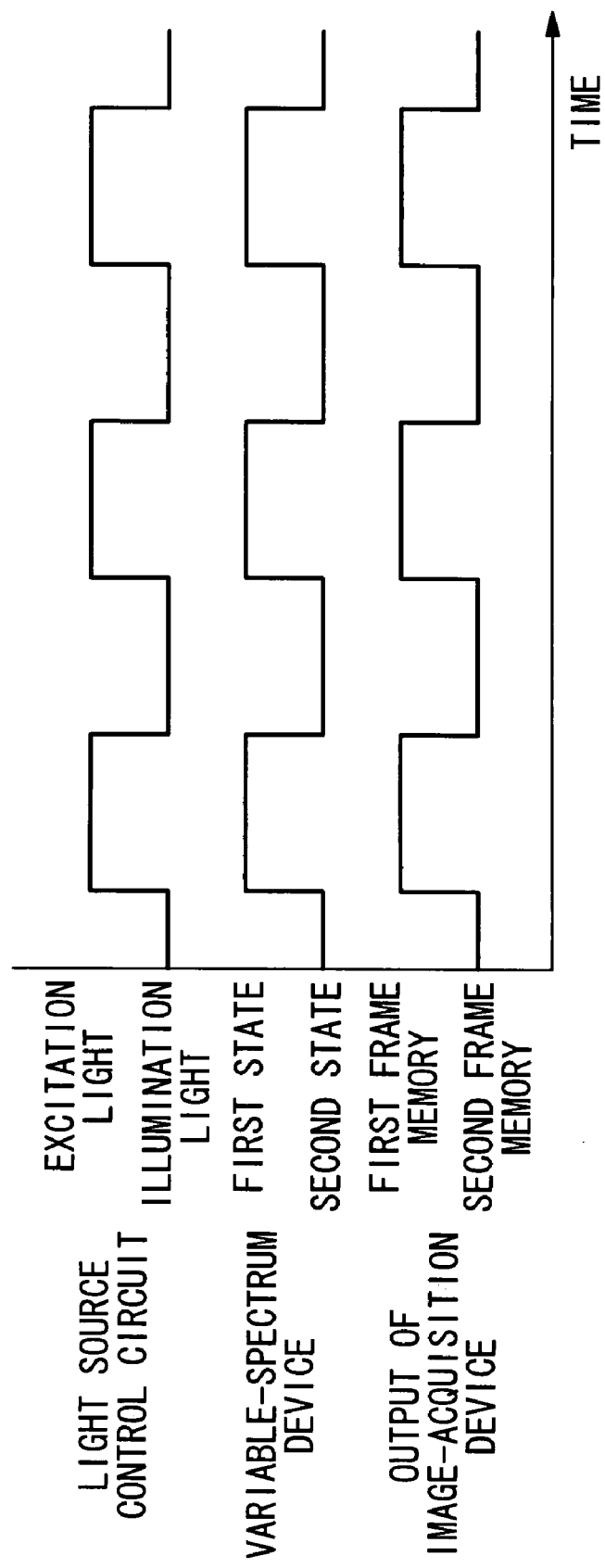
FIG. 4 is a timing chart illustrating the operation of the endoscope system shown in FIG. 1.

More specifically, as shown in the timing chart in FIG. 4, when excitation light is emitted from the excitation light source 9 by the operation of the light source control circuit 10, the variable-spectrum-device control circuit 19 puts the variable-spectrum device 13 into the first state and the image-acquisition-device driving circuit 18 causes image information from the image-acquisition device 14 to be output to a first frame memory 20a. When illumination light is emitted from the illumination light source 8, the variable-spectrum-device control circuit 19 puts the variable-spectrum device 13 into the second state and the image-acquisition-device driving circuit 18 causes image information from the image-acquisition device 14 to be output to a second frame memory 20b.

The image-processing circuit 21, for example, receives from the first frame memory 20a fluorescence image information obtained by the irradiation of the excitation light and outputs the information to a first channel of the display unit 6. The image-processing circuit 21 also receives from the second frame memory 20b reflected-light image information obtained by the irradiation of the illumination light and outputs the information to a second channel of the display unit 6.

The operation of the endoscope system 1 according to this embodiment, having the above structure, will now be described.

In order to acquire an image of an observation target A in the body cavity of a living organism using the endoscope system 1 of this embodiment, a fluorescent agent is injected into the body, and the insertion portion 2 is then inserted into the body cavity so that the tip 2a of the insertion portion 2 faces the observation target A in the body cavity. In this state, the light source unit 4 and the control unit 5 are operated. The illumination light source 8 and the excitation light source 9 are alternately operated under the control of the light source control circuit 10, thus generating illumination light and excitation light.

The illumination light and excitation light generated in the light source unit 4 are transmitted to the tip 2a of the insertion portion 2 via the light guide 7 and are irradiated from the tip 2a of the insertion portion 2 onto the observation target A.

When the observation target A is irradiated with the excitation light, the fluorescent agent permeated throughout the observation target A is excited, thereby emitting fluorescence. The fluorescence emitted from the observation target A is collected by the image-acquisition optical system 11 of the image-acquisition unit 3, passes through the barrier filter 12, and is incident on the variable-spectrum device 13.

The variable-spectrum device 13 is switched to the first state by the operation of the variable-spectrum-device control circuit 19 in synchronization with the operation of the excitation light source 9. Therefore, the transmittance with respect to the fluorescence is increased, and the variable-spectrum device 13 can transmit the incident fluorescence. In this case, a part of the excitation light component irradiated onto the observation target A is reflected at the observation target A and enters the image-acquisition unit 3 together with the fluorescence. However, because of the presence of the barrier filter 12 in the image-acquisition unit 3, the excitation light is blocked, thus preventing the excitation light from entering the image-acquisition device 14.

The fluorescence passing through the variable-spectrum device 13 is incident on the image-acquisition device 14, and fluorescence image information is acquired. The acquired fluorescence image information is stored in the first frame memory 20a, output on the first channel of the display unit 6 by the image-processing circuit 21, and displayed on the display unit 6.

On the other hand, when the observation target A is irradiated with the illumination light, the illumination light is reflected at the surface of the observation target A, collected by the image-acquisition optical system 11, passes through the barrier filter 12, and is incident on the variable-spectrum device 13. Since the wavelength band of the reflected light of the illumination light is located in the fixed transmission band of the variable-spectrum device 13, all of the reflected light component incident on the variable-spectrum device 13 is transmitted therethrough.

The reflected light passing through the variable-spectrum device 13 is incident on the image-acquisition device 14, and reflected-light image information is acquired. The acquired reflected-light image information is stored in the second frame memory 20*b*, output on the second channel of the display unit 6 by the image-processing circuit 21, and displayed on the display unit 6.

In this case, the variable-spectrum device 13 is switched to the second state by the operation of the variable-spectrum-device control circuit 19 in synchronization with the operation of the illumination light source 8. Therefore, the transmittance with respect to the fluorescence is decreased. Even when fluorescence enters, the variable-spectrum device 13 blocks the fluorescence. Accordingly, only the reflected light is acquired by the image-acquisition device 14.

As described above, the endoscope system 1 of this embodiment can provide the user with a fluorescence image and a reflected-light image.

According to the endoscope system 1 of this embodiment, the sensors 16 are provided in the variable-spectrum device 13. Accordingly, in the above case, when the variable-spectrum device 13 is switched between the first state and the second state, the distance between the two optical elements 13*a* and 13*b* is detected by the sensors 16, and voltage signals applied to the actuators 13*c* are subjected to feedback control. Consequently, the distance between the optical elements 13*a* and 13*b* can be controlled accurately, and light in a desired wavelength band can be spectrally dispersed with high accuracy, thus producing sharp fluorescence images and reflected-light images.

Furthermore, in this embodiment, electrical signals that are output from the sensor electrodes 16*a* and 16*b* and that represent the capacitance between the sensor electrodes 16*a* and 16*b* are amplified by the electrical circuit 17, which is fixed to the optical element 13*a* of the variable-spectrum device 13, and the output impedance thereof is decreased. The electrical signals are then transmitted to the insertion portion 2. Thus, the electrical signals are transmitted from the rear end of the insertion portion 2 to the variable-spectrum-device control circuit 19 disposed outside the body. Accordingly, crosstalk noise of the electrical signals detected by the sensors 16 can be reduced. This is advantageous in that the distance between the optical elements 13*a* and 13*b* can be detected with high accuracy, and the spectral characteristics of the variable-spectrum device 13 can be controlled with high accuracy.

The following various modifications and changes can be made in the endoscope system 1 of this embodiment.

Figure 6:
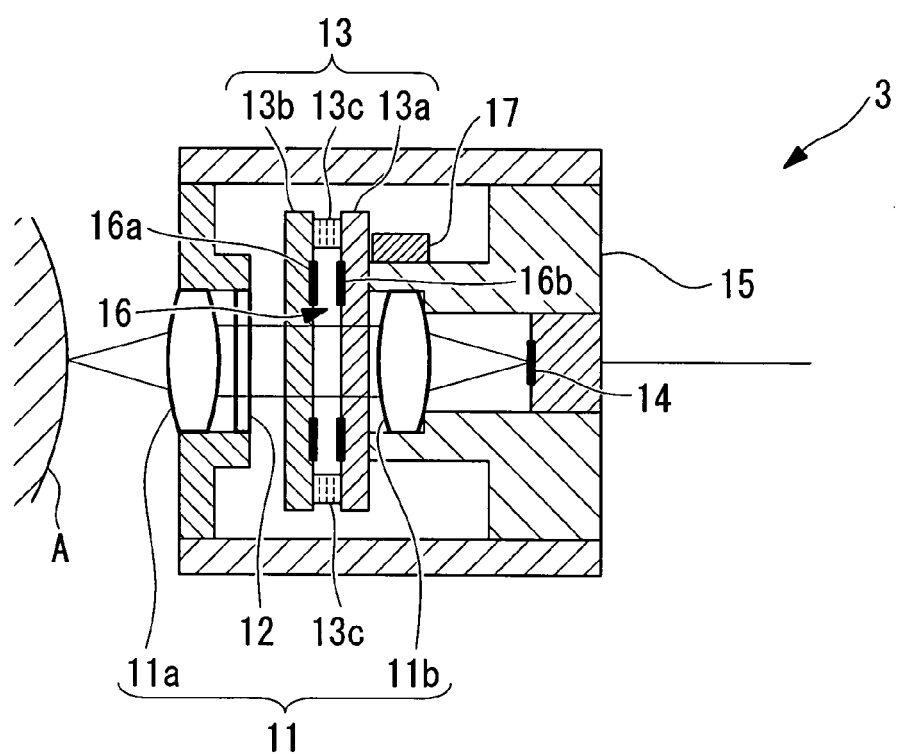
FIG. 6 is a longitudinal sectional view that schematically shows a modification of the image-acquisition unit shown in FIG. 2.

First, as shown in FIG. 6, instead of directly fixing the electrical circuit 17 to the optical element 13*a*, the electrical circuit 17 may be fixed to the frame structure 15 so as to be adjacent to the optical element 13*a*. In this case, the electrical circuit 17 is disposed at a position overlapping the optical element 13*a* (i.e., a position outside the effective optical diameter of the optical element 13*a*) as viewed from the optical axis direction. Accordingly, an increase in the outer diameter of the tip of the insertion portion 2 can be prevented, while disposing the electrical circuit 17 close to the sensors 16. By disposing the electrical circuit 17 closer to the rear end of the insertion portion 2 than the variable-spectrum device 13, the length of wiring in the insertion portion 2 can be decreased, thus further improving the effect of noise reduction.

A circuit that detects a capacitance as a voltage signal and that amplifies the signal is used as the electrical circuit 17, but the electrical circuit 17 is not limited thereto. A buffer circuit that does not have an amplifying function may be used. An example of the buffer circuit is a voltage follower circuit. The use of such a buffer circuit can also decrease the output impedance of the sensor output, and noise tolerance can be improved.

Figure 7A:
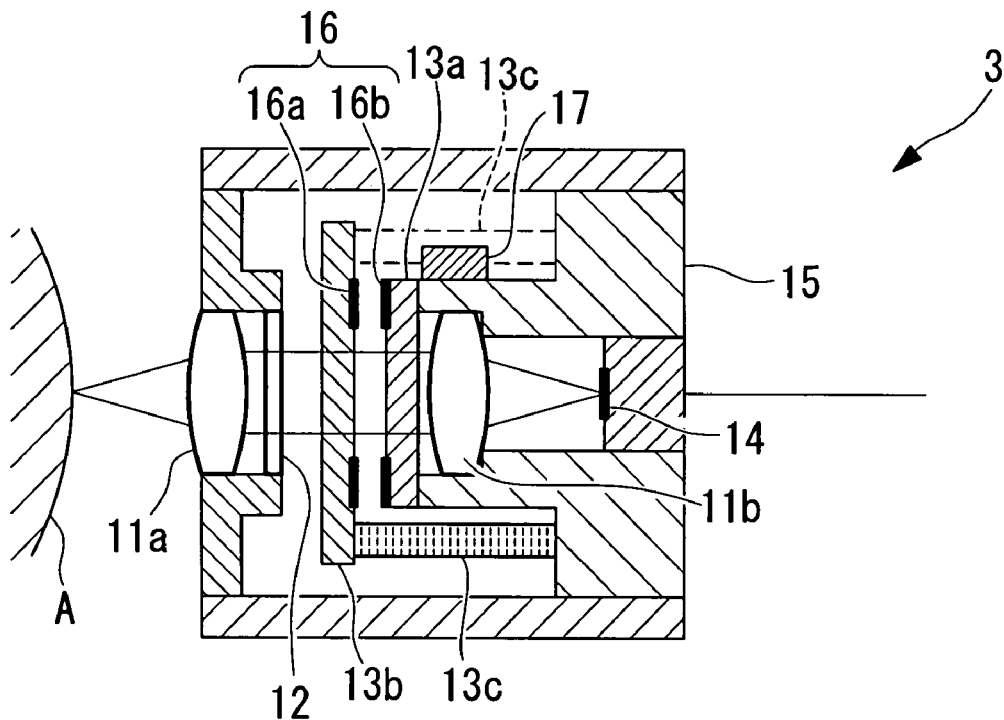
FIG. 7A is a longitudinal sectional view that schematically shows another modification of the image-acquisition unit shown in FIG. 2.
Figure 7B:
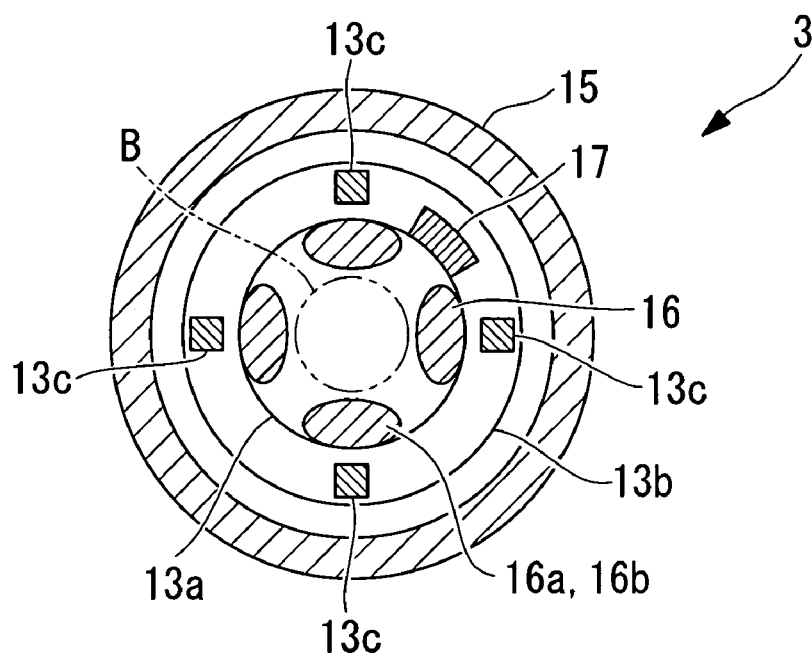
FIG. 7B is a transverse sectional view that schematically shows another modification of the image-acquisition unit shown in FIG. 2.

Alternatively, as shown in FIGS. 7A and 7B, when a plurality of actuators 13*c* of the variable-spectrum device 13 are disposed between the optical element 13*b* and the frame structure 15 at intervals in the circumferential direction, the electrical circuit 17 may be provided in a space between the actuators 13*c*. In this structure, since the space between the actuators 13*c* can be utilized, an increase in the outer diameter of the tip of the insertion portion 2 can be prevented.

Figure 8:
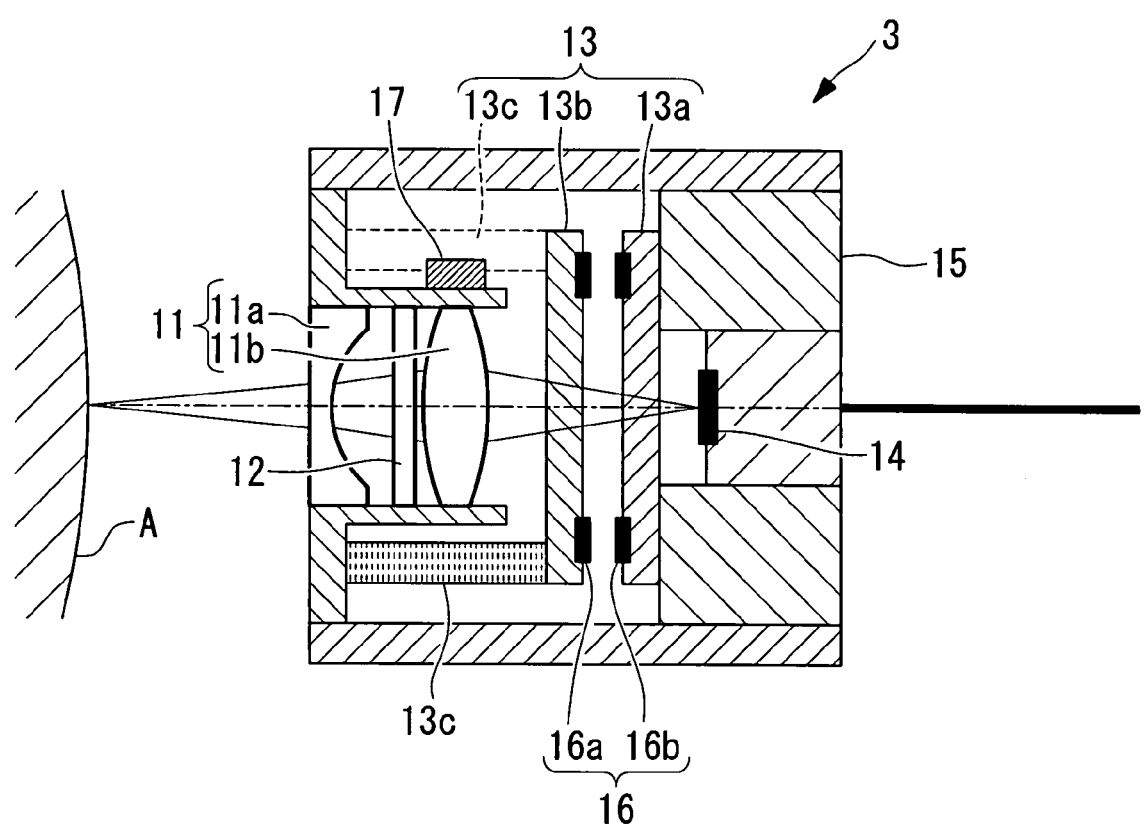
FIG. 8 is a longitudinal sectional view that schematically shows another modification of the image-acquisition unit shown in FIG. 2.

Alternatively, as shown in FIG. 8, when the structure of the image-acquisition optical system 11 is different from the above-described structure, namely, when a plurality of actuators 13*c* are disposed between the optical element 13*b* and the frame structure 15 fixing the image-acquisition optical system 11 at intervals in the circumferential direction, the electrical circuit 17 may be provided in a space between the actuators 13*c*, the space being disposed closer to the leading end than the variable-spectrum device 13.

Figure 9:
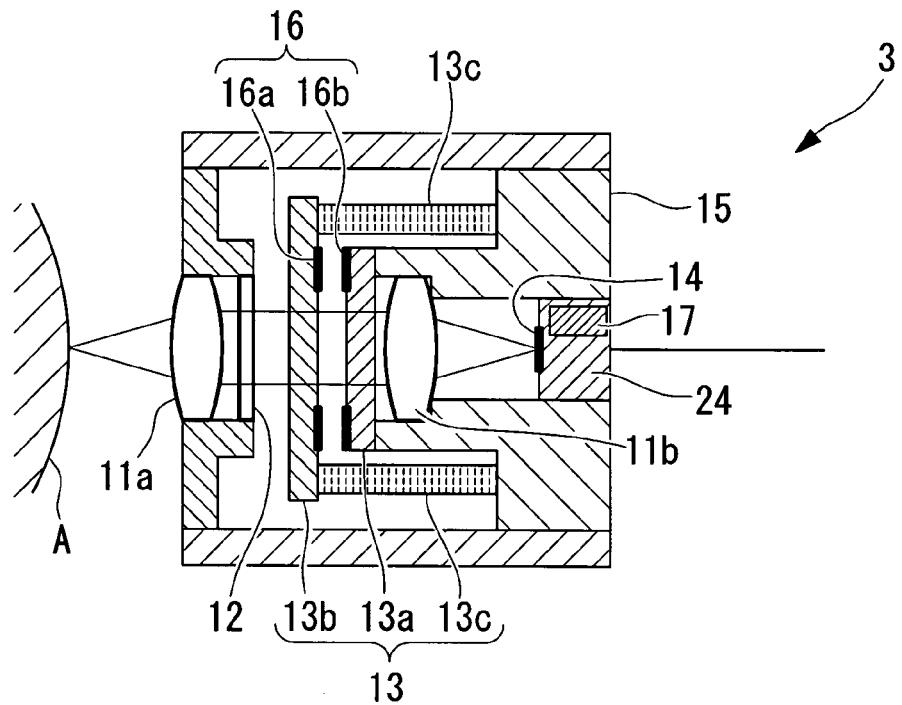
FIG. 9 is a longitudinal sectional view that schematically shows another modification of the image-acquisition unit shown in FIG. 2.

Alternatively, as shown in FIG. 9, the electrical circuit 17 for the sensors 16 may be provided on a circuit board (substrate) 24 for the image-acquisition device 14. When the circuit board 24 is shared, the volume of the image-acquisition unit 3 can be reduced to realize a reduction in size, compared with the case where a circuit board for mounting the electrical circuit 17 for the sensors 16 and the circuit board 24 for mounting an electrical circuit of the image-acquisition device 14 are separately provided.

Figure 10:
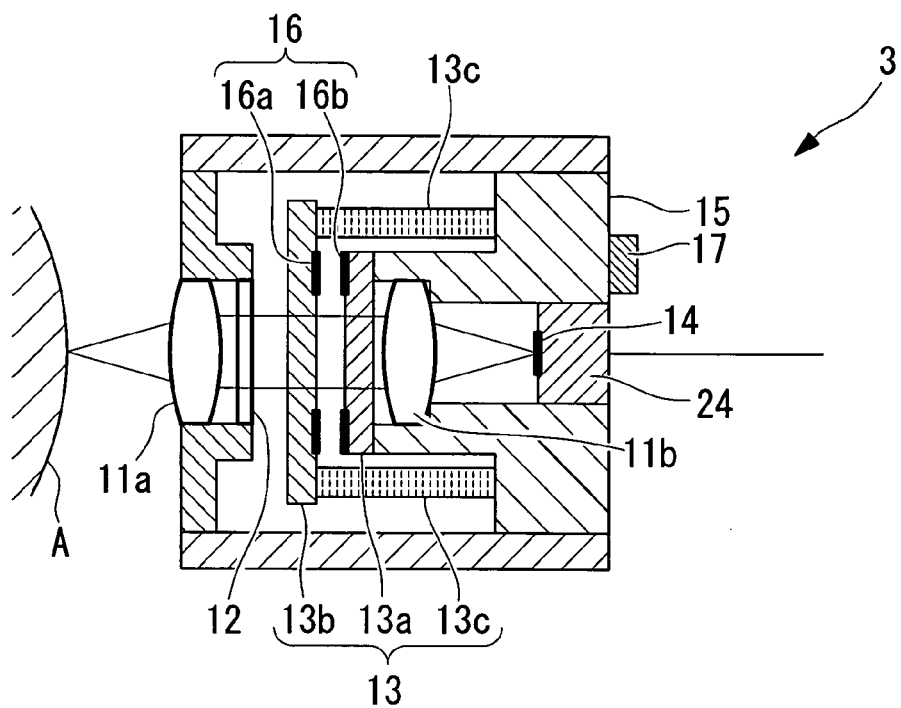
FIG. 10 is a longitudinal sectional view that schematically shows another modification of the image-acquisition unit shown in FIG. 2.

Alternatively, as shown in FIG. 10, the electrical circuit 17 may be provided outside the image-acquisition unit 3. Although the distance between the sensors 16 and the electrical circuit 17 is somewhat increased, by disposing the electrical circuit 17 outside the image-acquisition unit 3 where a sufficient space can be provided, an advantage is afforded in that mounting of the electrical circuit 17 can be easily performed.

In the endoscope system 1 of this embodiment, a system for acquiring a agent-fluorescence image and a reflected-light image has been described. Alternatively, the endoscope system 1 can be used for other combinations, such as an autofluorescence image and a agent-fluorescence image, and an autofluorescence image and a reflected-light image.

A circuit that converts a capacitance into a voltage value is used as the electrical circuit 17 for the sensors 16, but a circuit that converts a capacitance into a current value may also be used.

Furthermore, the electrical circuit 17 shown in FIG. 5 is provided at the tip of the insertion portion, but the structure is not limited thereto. Only the operational amplifier 22 may be provided at the tip of the insertion portion, and the AC power supply 23 may be provided outside the insertion portion.

Capacitance-type sensors are used as the sensors 16, but the sensors 16 are not limited thereto. For example, an eddy-current sensor (not shown) may also be used. The eddy-current sensor is operated as follows: A coil is provided on one of the facing optical elements 13*a* and 13*b*, and a metal plate is provided on the other optical element so that the coil and the metal plate face each other. A high-frequency magnetic field is generated by a resonant circuit including a coil and a capacitor, thereby generating eddy current in an object. The displacement of the optical element 13a is measured by utilizing a characteristic whereby the magnetic field changes depending on the eddy current.

In this embodiment, a description has been made using an endoscope system 1 having the bending portion 2b as an example. Alternatively, the endoscope system 1 may be applied to a rigid scope not having a bending portion 2b. The observation target is not limited to a living organism. The endoscope system 1 can also be applied to an industrial endoscope for observing the insides of piping, machines, structures, and so forth.

An endoscope system according to a second embodiment of the present invention will now be described with reference to FIGS. 11 and 12.

In the description of this embodiment, portions having the same structure as those of the endoscope system 1 of the above-described first embodiment are assigned the same reference numerals, and a description of the common structure is omitted.

In the endoscope system 1 of the first embodiment, the variable-spectrum device 13 is provided in the image-acquisition unit 3. In contrast, in an endoscope system 31 of this embodiment, the variable-spectrum device 13 is provided in a part of a light source unit 32.

Figure 11:
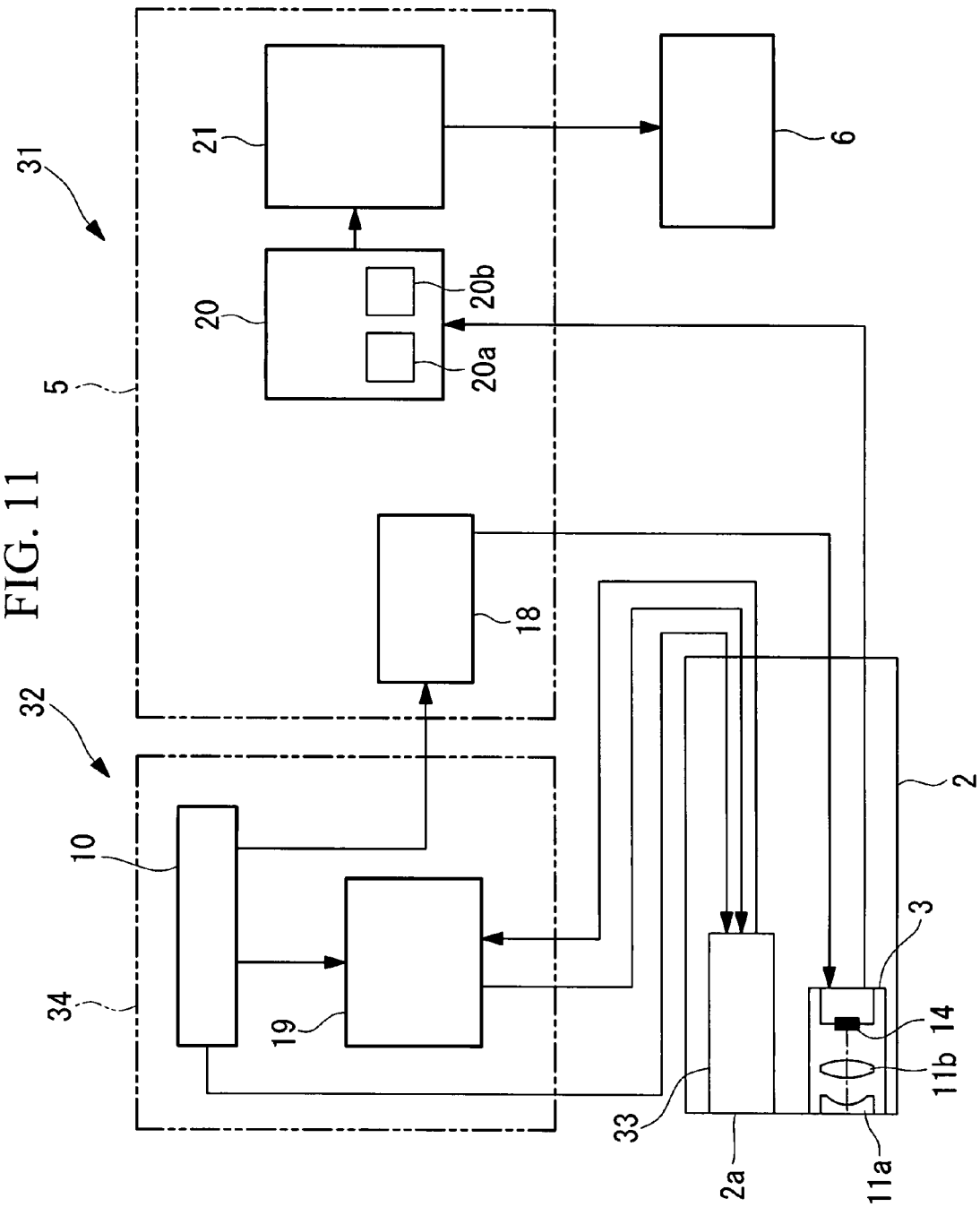
FIG. 11 is a block diagram showing the overall structure of an endoscope system according to a second embodiment of the present invention.

More specifically, as shown in FIG. 11, the light source unit 32 includes a leading-end light-source portion 33 disposed at the tip of an insertion portion 2 and a light-source control unit 34 that is disposed outside the body and that controls the leading-end light-source portion 33.

Figure 12:
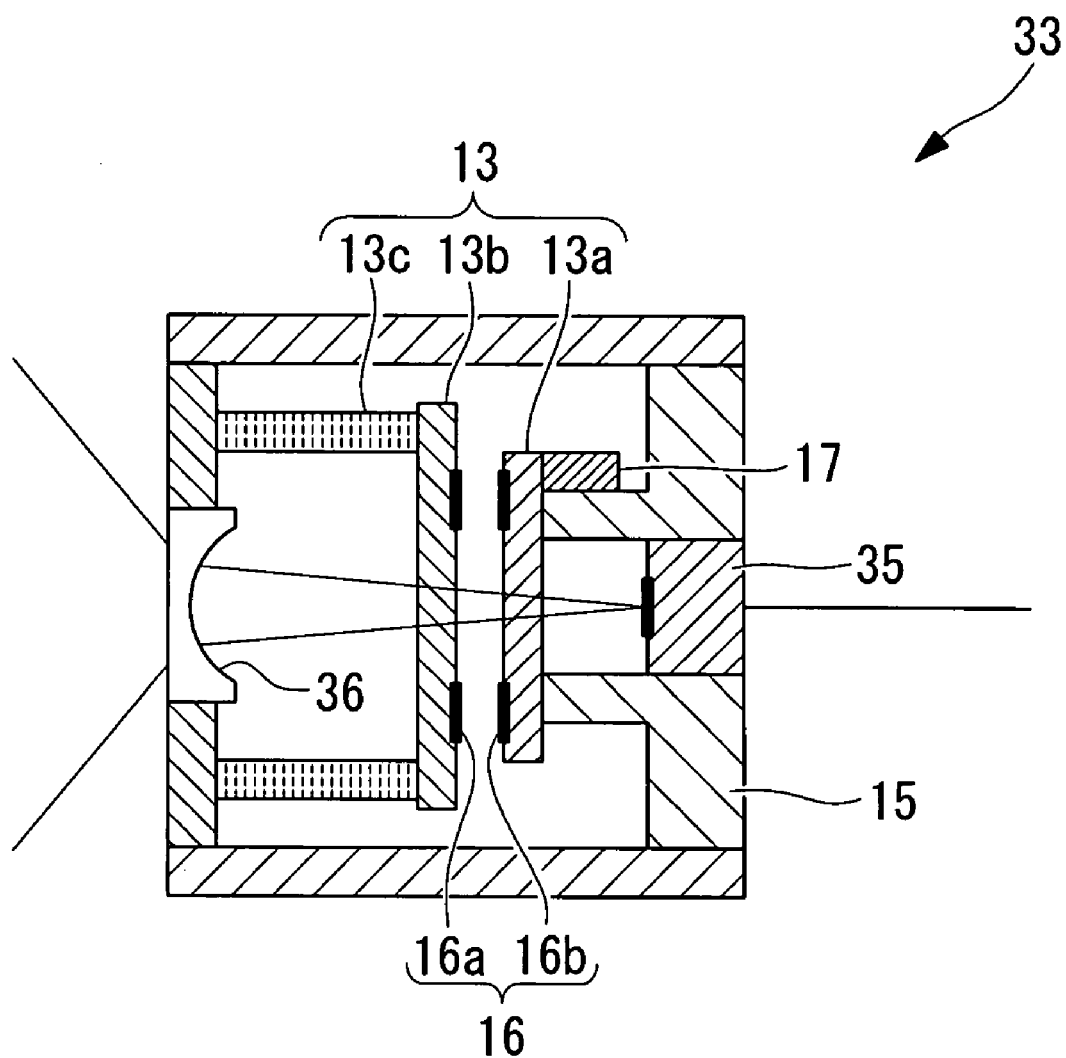
FIG. 12 is a longitudinal sectional view that schematically shows an image-acquisition unit of the endoscope system shown in FIG. 11.

As shown in FIG. 12, the leading-end light-source portion 33 includes a white LED (photoelectric transducer: light source) 35 that emits white light; the variable-spectrum device 13 including two optical elements 13a and 13b, and actuators 13c; a lens 36 that diverges the white light emitted from the white LED 35; and a frame structure 15 to which these components are secured.

The actuators 13c are disposed between the optical element 13b and the frame structure 15.

An electrical circuit 17 is fixed to the fixed optical element 13a. The electrical circuit 17 converts a capacitance detected by sensors 16, each having sensor electrodes 16a and 16b, provided on the variable-spectrum device 13 into a voltage signal and amplifies the signal. In this structure, the length of wiring connecting the sensor electrodes 16a and 16b to the electrical circuit 17 can be minimized. Consequently, crosstalk noise can be suppressed, and the distance between the optical elements 13a and 13b can be controlled with high accuracy. As a result, a living organism A can be irradiated with illumination light in a desired wavelength band with a high transmittance, thus acquiring a bright and sharp spectral image.

The leading-end light-source portion 33 includes a single white LED 35. Alternatively, the leading-end light-source portion 33 may include a plurality of white LEDs 35 in order to increase the amount of illumination light and to improve light distribution characteristics. Alternatively, a single white LED 35 and a diffusing plate may be used in combination so as to increase the light source area. Alternatively, a lamp or the like may be used.

Alternatively, a multi-wavelength excitation semiconductor laser, a superluminescent diode, or the like may also be used.

The arrangement of the electrical circuit 17 is not limited to that shown in FIG. 12. The same arrangements as those described in the first embodiment shown in FIGS. 6 to 10 can be selected. For example, as shown in FIGS. 7A and 7B, the electrical circuit 17 may be provided in a space between the actuators 13c disposed at intervals in the circumferential direction. This structure is advantageous in that crosstalk noise can be decreased while preventing an increase in the outer diameter of the tip of the insertion portion 2.

What is claimed is:

1. An endoscope system, at least a portion of which is to be inserted into the body cavity of a living organism and which acquires an image of an observation target in the body cavity, comprising, at a leading end of the portion inserted into the body cavity:
   a variable-spectrum device whose spectral characteristics are changed by changing a gap between two facing optical elements that are separated by the gap;
   an actuator that changes the gap between the two optical elements in accordance with an input driving signal;
   a sensor that detects the gap between the two optical elements, wherein the sensor comprises a plurality of electrodes provided on the two optical elements, and the gap between the two optical elements is detected by detecting the capacitance between the electrodes; and
   an electrical circuit that adjusts errors in the inclination of the two optical elements on the basis of signals output from the plurality of electrodes.

2. The endoscope system according to claim 1, wherein the electrical circuit comprises an amplifying circuit.

3. The endoscope system according to claim 1, wherein the electrical circuit comprises a buffer circuit.

4. The endoscope system according to claim 1, wherein the sensor comprises a coil provided on one of the two optical elements and a metal plate provided on the other optical element, and the gap between the two optical elements is detected by detecting the impedance of the coil.

5. The endoscope system according to claim 1, wherein the actuator comprises a piezoelectric element.

6. The endoscope system according to claim 1, further comprising a photoelectric transducer facing the variable-spectrum device.

7. The endoscope system according to claim 6, wherein the photoelectric transducer is a light source that converts an electrical signal into light.

8. The endoscope system according to claim 6, wherein the photoelectric transducer is a light-receiving device that converts light into an electrical signal.

9. The endoscope system according to claim 1, wherein the leading end is disposed closer to a tip than a portion that can be bent in order to change the orientation of the tip of the insertion portion.

10. The endoscope system according to claim 1, wherein the electrical circuit is disposed adjacent to the variable-spectrum device.

11. The endoscope system according to claim 1, wherein the electrical circuit is disposed closer to the rear end of the insertion portion than the variable-spectrum device.

12. The endoscope system according to claim 1, wherein the electrical circuit is disposed at a position that is shifted from the variable-spectrum device in the axial direction of the insertion portion and that overlaps the variable-spectrum device in the radial direction of the insertion portion.

13. The endoscope system according to claim 12, wherein a plurality of actuators are disposed around the axis of the insertion portion at intervals in the circumferential direction thereof, and the electrical circuit is disposed in a space between the actuators.

14. The endoscope system according to claim 6, wherein the electrical circuit is provided on a substrate of the photoelectric transducer.

15. The endoscope system according to claim 6, wherein the electrical circuit is disposed closer to the leading end of the insertion portion than the photoelectric transducer.

16. The endoscope system according to claim 1, wherein one of the two optical elements is fixed to the portion inserted into the body cavity, and the electrical circuit is fixed to the one fixed optical element.

* * * * *